United States Patent [19]

Nakane

[11] Patent Number: 4,592,631
[45] Date of Patent: Jun. 3, 1986

[54] CAMERA-EQUIPPED OPHTHALMOSCOPE

[75] Inventor: Toshiaki Nakane, Tokyo, Japan

[73] Assignee: Asahi Kogaku Kogyo Kabushiki Kaisha, Tokyo, Japan

[21] Appl. No.: 663,852

[22] Filed: Oct. 22, 1984

[30] Foreign Application Priority Data

Nov. 2, 1983 [JP] Japan .................. 58-170557[U]

[51] Int. Cl.[4] .............................................. A61B 3/14
[52] U.S. Cl. ..................................... 351/206; 350/255; 351/205
[58] Field of Search ................. 351/205, 206; 350/255

[56] References Cited

U.S. PATENT DOCUMENTS 4,018,514 4/1977 Plummer ........................... 351/206

Primary Examiner—Rodney B. Bovernick
Assistant Examiner—P. M. Dzierzynski
Attorney, Agent, or Firm—Hill, Van Santen, Steadman & Simpson

[57] ABSTRACT

In a camera-equipped ophthalmoscope, an aspherical objective lens is connected to one end of a cord wound about a cord-roll-up drum biased by a helical spring to rotate in a direction to take up the cord. The rotation of the cord-roll-up drum causes a lens-barrel contained therein to move in the direction of its optical axis, whereby the focus of the photographing lens is corrected depending upon the amount of the movement of the aspherical objective lens.

4 Claims, 2 Drawing Figures

CAMERA-EQUIPPED OPHTHALMOSCOPE

BACKGROUND OF THE INVENTION

This invention relates to a camera-equipped ophthalmoscope.

To photograph a retina image of a patient with a camera-equipped ophthalmoscope, it is necessary to provide an aspheric lens at a suitable position between an eye to be diagnosed and the ophthalmoscope. However, since the aspheric lens is held by a hand of an operator, it is difficult to hold it at an optimum position and distance from the eye. Consequently, the lens is often held at a position on the outside of the focus of a photogrtaphing lens, which causing bluring.

SUMMARY OF THE INVENTION

Accordingly, it is an object of this invention to provide an improved camera-equipped ophthalmoscope capable of automatically correcting the focus of a photographing lens in accordance with variation of the position of an aspheric lens.

According to this invention, there is provided a camera-equipped ophthalmoscope comprising a lens-barrel containing a lens and slidable in a direction of an optical axis, a lens-barrel being provided with a radially extending projection on the outer periphery thereof, a rotary drum concentric with the lens-barrel and provided with a helical groove on the inner surface thereof for receiving said projection, a cord-roll-up drum coaxial with the rotary drum and operatively connected thereto, a cord with one end secured to the cord-roll-up drum, and objective lens connected to the other end of the cord, whereby, according to the movement of the objective lens, the lens-barrel is slid in the direction of the optical axis so as to correct the focus.

DESCRIPTION OF THE PREFERRED EMBODIMENT

Figure 1:
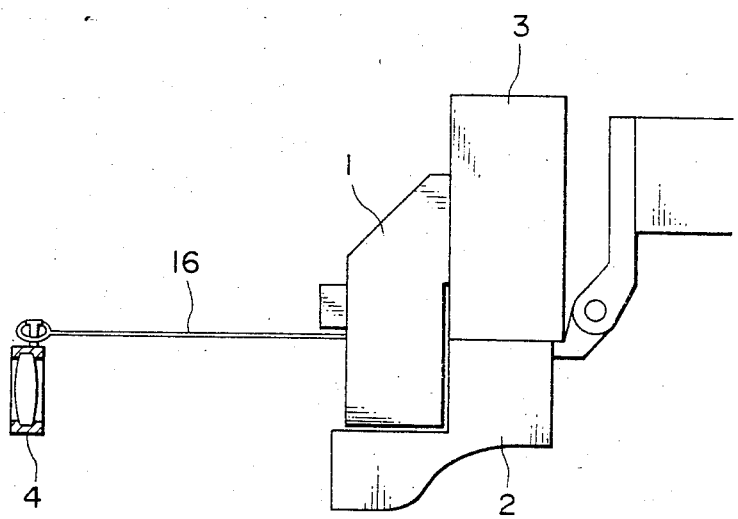
FIG. 1 shows a camera-equipped ophthalmoscope embodying the invention.

The ophthalmoscope illustrated in the accompanying drawings comprises a photographing lens unit 1, a binocular 2, a camera body 3, and an aspherical objective lens 4 which is used to diagnose and photograph the retina of an eye.

In the photographing lens unit 1, a lens-barrel 10 including a plurality of lenses is fitted in an inner cylinder 11 to be slidable in the direction of the optical axis, and a rotary drum 12 and a cord-roll-up drum 13 are mounted on the outer periphery of the inner cylinder 11 to be relatively rotatable.

Flange gears 12a and 13a having different diameters are formed on the respective opposing ends of the rotary drum 12 and the cord-roll-up drum 13. On the other hand, gears 15a and 15b having different diameters are secured to the upper and lower ends of a shaft 14 which is rotatably supported by a projection 11a of the inner cylinder 11. The gears 12a and 13a respectively mesh with the gears 15a and 15b so as to rotate each other at a predetermined ratio of rotation.

The rotary drum 12 and the lens-barrel 10 are coupled together by a pin 10a secured to the outer periphery of the lens-barrel 10 and received in a slot 11b provided for the inner cylinder 11. The outer end of the pin 10a engages a helical groove formed on the inner surfaceof the rotary drum 12. Accordingly, as the rotary drum 12 rotates, the lens-barrel 10 slides in the inner cylinder 11 along the optical axis.

Figure 2:
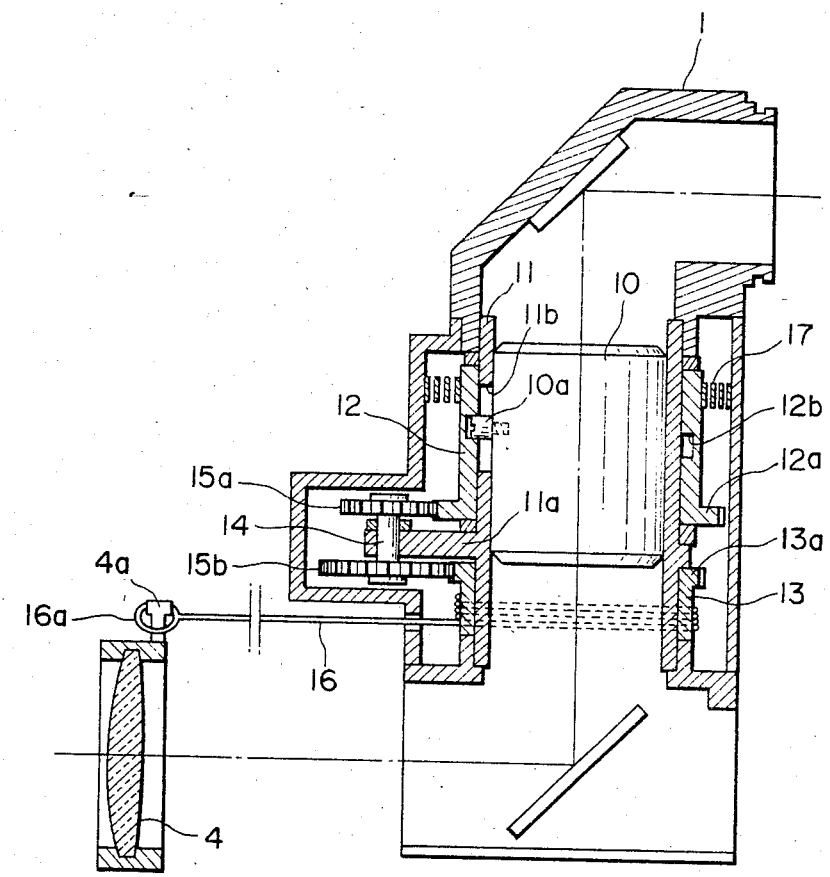
FIG. 2 is an enlarged sectional view of the photographing lens unit.

A cord 16 having a loop 16a at the outer end is wound about the cord-roll-up drum 13 so that the drum 13 is rotated as the loop 16 moves to the right or left as viewed in FIG. 2.

One end of a spiral spring 17 is secured to the inner wall of the photographing lens unit 1, and the other end of the spring 17 is secured to the outer periphery of the rotary drum 12 so as to bias the cord-roll-up drum 13 in the take up direction via rotary drum 12 and gears 15a and 15b. A hook 4a adapted to engage the loop 16a at the fore end of the cord 16 is provided for a lens-supporting frame so that the cord 16 is payed out or taken up as the position of the aspherical lens 4 changes.

The ratio of rotations between the cord-roll-up drum 13 and the rotary drum 12 coupled through gears 15a and 15b, and the ratio of relative positions, in the direction of the optical axis, between the rotary drum 12 and the lens-barrel 10 coupled by the pin 10a and the helical groove 12b, are present such that the variation in the length of the movement of the cord 16 and the amount of sliding of the lens-barrel in the direction of the optical axis caused by the movement of the cord 16 would correspond to the variation of the position of the aspherical lens 4 and to the amount of correction of the focal distance between a photographing lens and a photographic film.

In the operation, when the aspherical objective lens 4 is held at a position easy to photograph the retina image of a patient after engaging the loop 16a with the hook 4a, the lens-barrel 10 would slide in the direction of the optical axis by the amount corresponding to the amount of the movement of the cord 16 so as to automatically correct the focus.

As above described, with the camera-equipped ophthalmoscope embodying the invention, during photographing the retina image of a patient, an optimum focus can always be assured by merely holding the aspherical objective lens near a photographing position after connecting the fore end of the cord to the lens supporting frame, which assuring rapid and accurate photographing.

What is claimed is:

1. A camera-equipped ophthalmoscope comprising:
   a lens-barrel containing a lens and slidable in a direction of an optical axis, said lens-barrel being provided with a radially extending projection on the outer periphery thereof;
   a rotary drum concentric with said lens-barrel and provided with a helical groove on the inner surface thereof for receiving said projection;
   a cord-roll-up drum coaxial with said rotary drum and operatively connected thereto;
   a cord with one end secured to said cord-roll-up drum; and
   an objective lens connected to the other end of said cord,
   whereby, according to the movement of said objective lens, said lens-barrel is slid in the direction of said optical axis so as to correct the focus.

2. The ophthalmoscope according to claim 1 wherein said cord-roll-up drum and said rotary drum are coupled together through a gear train, and wherein a spiral spring is interposed between said rotary drum and a casing so as to bias said cord-roll-up drum to rotate in a direction to take up said cord.

3. The ophthalmoscope according to claim 1 wherein said objective lens is an aspherical lens supported by a frame, said frame being provided with a hook adapted to engage with a loop formed at said other end of the cord.

4. The ophthalmoscope according to claim 1 which further comprises a cylindrical member interposed between said rotary drum and said lens-barrel, said cylindrical member being formed with a longitudinal slot for guiding said projection.

* * * * *